(12) United States Patent
Wang et al.

(10) Patent No.: US 9,031,292 B2
(45) Date of Patent: May 12, 2015

(54) METHOD FOR THE DIAGNOSIS OF NEURODEGENERATIVE DISORDER BY USING DIFFUSION KURTOSIS IMAGING

(75) Inventors: Jiun-Jie Wang, Tao-Yuan (TW); Wey-Yil Lin, Tao-Yuan (TW); Chin-Song Lu, Tao-Yuan (TW); Yi-Hsin Weng, Tao-Yuan (TW); Ren-Hsiang Hsieh, Tao-Yuan (TW); Shu-Hang Ng, Tao-Yuan (TW); Yau-Yau Wai, Tao-Yuan (TW); Yung-Liang Wan, Tao-Yuan (TW)

(73) Assignee: Chang Gung University, Tao-Yuan (TW)

( * ) Notice: Subject to any disclaimer, the term of this patent is extended or adjusted under 35 U.S.C. 154(b) by 286 days.

(21) Appl. No.: 13/450,939

(22) Filed: Apr. 19, 2012

(65) Prior Publication Data

US 2013/0279771 A1 Oct. 24, 2013

(51) Int. Cl.
*G06K 9/00* (2006.01)
*A61B 5/00* (2006.01)
*A61B 5/055* (2006.01)
*G06T 7/00* (2006.01)
*G01R 33/563* (2006.01)

(52) U.S. Cl.
CPC ............ *A61B 5/4082* (2013.01); *A61B 5/055* (2013.01); *G06T 7/0012* (2013.01); *G06T 2207/10016* (2013.01); *G06T 2207/10092* (2013.01); *G06T 2207/30016* (2013.01); *G01R 33/56341* (2013.01)

(58) Field of Classification Search
USPC ....................................................... 382/128
See application file for complete search history.

(56) References Cited

U.S. PATENT DOCUMENTS

2010/0303813 A1* 12/2010 Carulli et al. .............. 424/134.1

OTHER PUBLICATIONS

Jens H. Jensen, Joseph A. Helpern, Anita Ramani, Hanzhang Lu, and Kyle Kaczynski; Diffusional Kurtosis Imaging: The Quantifcation of Non-Gaussian Water Diffusion by Means of Magnetic Resonance Imaging; Magnetic Resonance in Medicine 53, 2005, pp. 1432-1440.*
Khachaturian et al., "Focal Reversible Deactivation of Cerebral Metabolism Affects Water Diffusion", National Institute of Health, 2008 Wiley-Liss, Inc.*
Cauter et al., "Gliomas: Diffusion Kurtosis MR Imaging in Grading" Radiology, Mar. 28, 2012.*
Jens H. Jensen and Joseph A. Helpern, "MRI Quantification of Non-Gaussian Water Diffusion by Kurtosis Analysis", NIH, NMR Biomed. Aug. 2010.*
Joachim Graessner, "Frequently Asked Questions: Diffusion-Weighted Imaging (DWI)" Jan. 2011, Retrieved from the internet on Aug. 22, 2014 from URL: http://www.healthcare.siemens.com/siemens_hwem-hwem_ssxa_websites-context-root/wcm/idc/siemens_hwem-hwem_ssxa_websites-context-root/wcm/idc/groups/public/@global/@imaging/@mri/documents/download/mdaw/mdey/~edisp.*
Jens H. Jensen and Joseph Helpern, "MRI Quantification of Non-Gaussian Water Diffusion by Kurtosis Analysis", Aug. 2010, Retrieved from the internet on Aug. 22, 2014 from URL:<http://www.ncbi.nlm.nih.gov/pmc/articles/PMC2997680/pdf/nihms251449.pdf>.*

(Continued)

*Primary Examiner* — Gregory F Cunningham
(74) *Attorney, Agent, or Firm* — Rosenberg, Klein & Lee

(57) ABSTRACT

The invention relates to the use of diffusion kurtosis imaging (DKI) in the diagnosis of Parkinson Disease related neurodegenerative disorders, including (but not limited to) Parkinson's disease (PD) and Parkinson plus syndromes.

15 Claims, 8 Drawing Sheets

(56) References Cited

OTHER PUBLICATIONS

J. Wang1, W. Lin2, C. Lu3, A. Tabesh4, Y. Weng5, and Y. Wai5, "Improved sensitivity and specificity in the diagnosis of Parkinson's Disease from Diffusion Kurtosis Imaging", 2011, Retrieved from the internet on Aug. 22, 2014 from URL:<http://cds.ismrm.org/protected/11MProceedings/files/2183.pdf>.*
Yoshikawa et al., "Early pathological changes in the parkinsonian brain demonstrated by diffusion tensor MRI", J Neurol Neurosurg Psychiatry 2004;75:481-484.*
Haiyin Chen, "Cerebellar and Cerebellar Thalamic Contributions to Motor Adaptation", The Johns Hopkins University, Mar. 2007.*
Rossor et al., "The diagnosis of young-onset dementia", NIH, Lancet Neurol. Aug. 2010.*
Benjamin A. Hoff et al. "Assessment of Multiexponential Diffusion Features as MRI Cancer Therapy Response Metrics", 2010, Retrieved from the Internet on Nov. 21, 2014 from <URL:http://deepblue.lib.umich.edu/bitstream/handle/2027.42/78223/22507_ftp.pdf?sequence=1>.*
David A. Bennett, M.D., Laurel A. Beckett, Ph.D., Anne M. Murray, M.D., M.SC., Kathleen M. Shannon, M.D., Christopher G. Goetz, M.D., David M. Pilgrim, M.D., and Denis A. Evans, M.D.; Prevalence of Parkinsonian Signs and Associated Mortality in a Community Population of Older People; The New England Journal of Medicine, Jan. 1996, vol. 334, No. 2, pp. 71-76.
Elan D. Louis, M.D., MS, Karen Marder, MD, MPH, Lucien Cote, MD, Ming Tang, PhD, Richard Mayeux, MD, MSE; Mortality from Parkinson Disease; Arch Neurol, Mar. 1997, vol. 54, pp. 260-264.
J.M. Gorell, MD, R.J. Ordidge, PhD, G.G. Brown, PhD, J-C. Deniau, MS, N.M. Buderer, MS, and J.A. Helpern, PhD; Increased Iron-Related MRI Contrast in the Substantia Nigra in Parkinson's Disease; Neurology, Jun. 1995, pp. 1138-1143.
L. Minati, M. Grisoli, F. Carella, T. Desimone, M.G. Bruzzone, M. Savoiardo; Imaging Degeneration of the Substantia Nigra in Parkinson Disease with Inversion-Recovery MR Imaging; AJNR AM J Neuroradiol 28:309-13; Feb. 2007; pp. 309-313.
E.O. Stejskal and J.E. Tanner; Spin Diffusion Measurements: Spin Echoes in the Presence of a Time Dependent Field Gradient; AIP; The Journal of Chemical Physics; 42, 288, 1965, pp. 288-292.
Stephen R. Rose, Fang Chen, Jonathan B. Chalk, Fernando O. Zelaya, Wendy E. Strugnell, Mark Benson, James Semple, David M. Doddrell; Loss of Connectivity in Alzheimer's Disease: An Evaluation of White Matter Tract Integrity with Colour Coded MR Diffusion Tensor Imaging; J Neurol Neurosurg Psychiatry 2000; 69 pp. 528-530.
D.J. Werring, MRCP, C.A. Clark, PhD, G.J. Barker, PhD, A.J. Thompson, FRCP, and D.H. Miller, FRCP, Diffusion Tensor Imaging of Lesions and Normal-Appearing White Matter in Multiple Sclerosis; Neurology, May 1, 1999, vol. 52, No. 8, pp. 1626-1632.
J.H. Jensen, J.A. Helpern; Quantifying Non-Gaussian Water Diffusion by Means of Pulsed-Field-Gradient MRI; Berkeley, CA International Society for Magnetic Resonance in Medicine, 2003, p. 2154.
Jens H. Jensen, and Joseph A. Helpern, MRI Quantification of Non-Gaussian Water Diffusion by Kurtosis Analysis; National Institutes of Health, NMR Biomed. Aug. 2010, 23(7), pp. 1-31.
Peter Raab, MD, Elke Hattingen, MD, Kea Franz, MD, Friedhelm E. Zanella, MD, Heinrich Lanfermann, MD; Cerebral Gliomas: Diffusional Kurtosis Imaging Analysis of Microstructural Differences; Radiology: vol. 254, No. 3, Mar. 2010, pp. 876-881.
Maria F. Falangola, PhD, Jens H. Jensen, PhD, James S. Babb, PhD, Caixia Hu, MS, Francisco X. Castellanos, MD, Adriana Di Martino, MD, Steven H. Ferris, PhD, and Joseph A. Helpern, PhD; Age-Related Non-Gaussian Diffusion Patterns in the Prefrontal Brain; Journal of Magnetic Resonance Imaging 28: 1345-1350 (2008).
Adolf Pfefferbaum, Edith V. Sullivan, Maj Hedehus, Kelvin O. Lim, Elfar Adalsteinsson, and Michael Moseley; Age-Related Decline in Brain White Matter Anisotropy Measured with Spatially Corrected Echo-Planar Diffusion Tensor Imaging; Magnetic Resonance in Medicine vol. 44 pp. 259-268 (2000).
Jiunjie Wang, PhD, Yauyau Wai, MD, Wey-Yil Lin, MD, Shuhang Ng, MD, Chi-Hong Wang, MD, Renhsiang Hsieh, BSc, Rou-Shayn Chen, MD, and Chin-Song Lu, MD; Microstructural Changes in Patients with Progressive Supranuclear Palsy: A Diffusion Tensor Imaging Study; Journal of Magnetic Resonance Imaging 32: pp. 69-75 (2010).
D.E. Vaillancourt, PhD, M.B. Spraker, BS, J. Prodoehl, PhD, PT, I. Abraham, D.M. Corcos, PhD, X.J. Zhou, PhD, C.L. Comella, MD, and D.M. Little, PhD; High-Resolution Diffusion Tensor Imaging in the Substantia Nigra of De Novo Parkinson Disease; 2009 Neurology 72(16); pp. 1378-1384.
L.L. Chan, H. Rumpel, K. Yap, E. Lee, H-V Loo, G-L Ho, S Fook-Chong, Y Yuen, E-K Tan; Case Control Study of Diffusion Tensor Imaging in Parkinson's Disease; 2007, Journal of Neurology, Neurosurgery & Psychiatry, 78(12); pp. 1383-1386.

\* cited by examiner

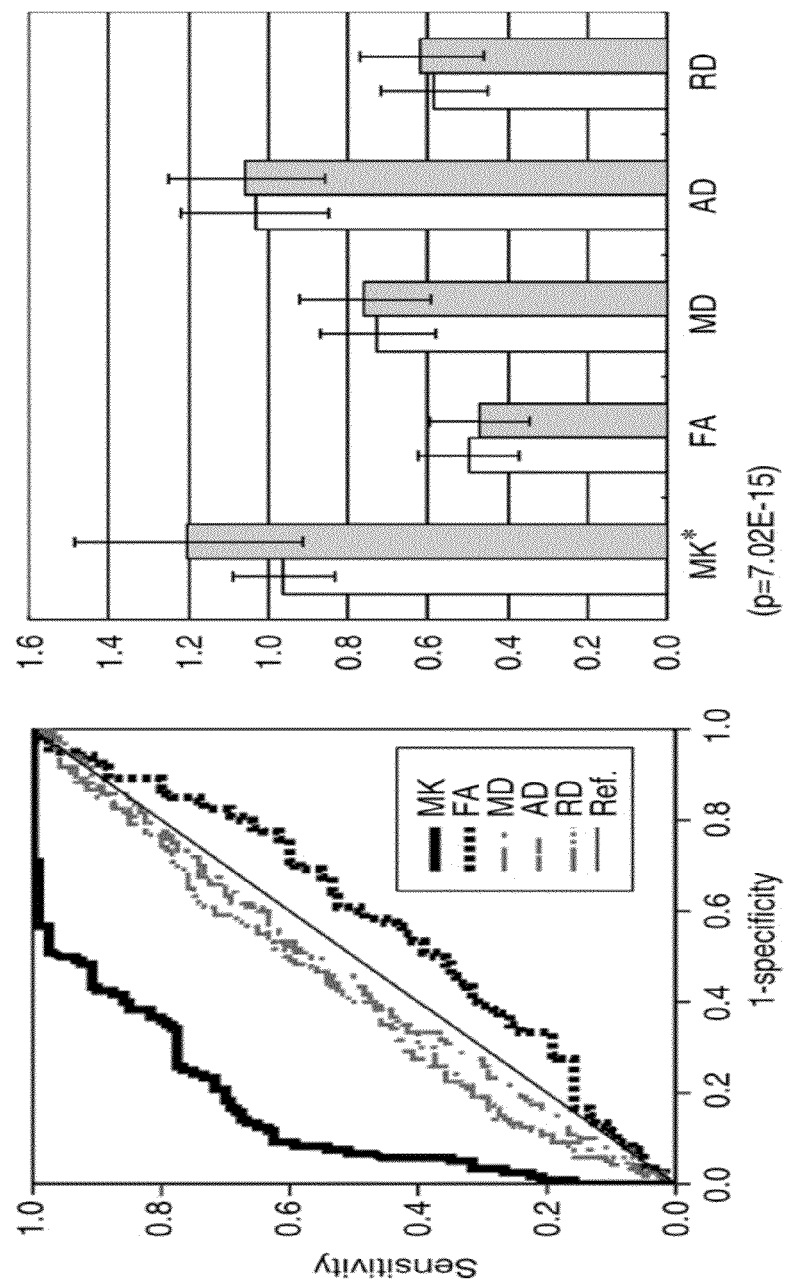

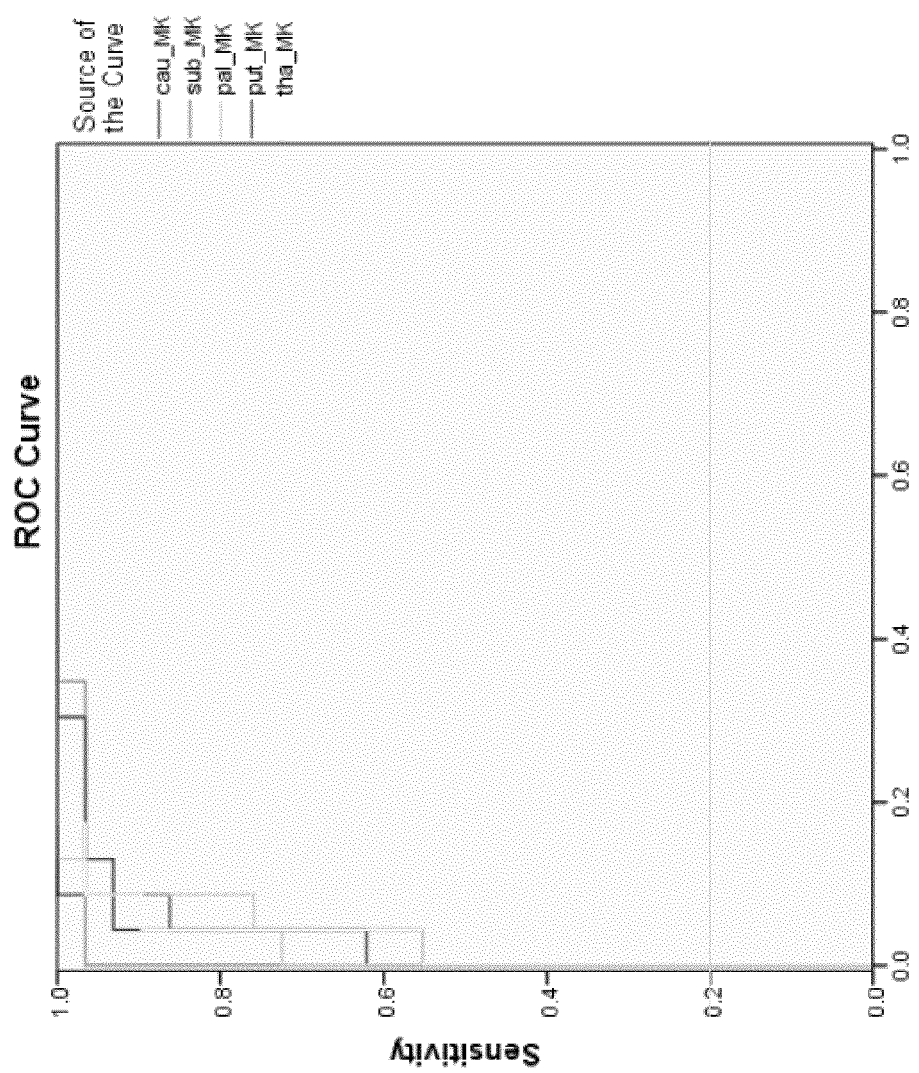

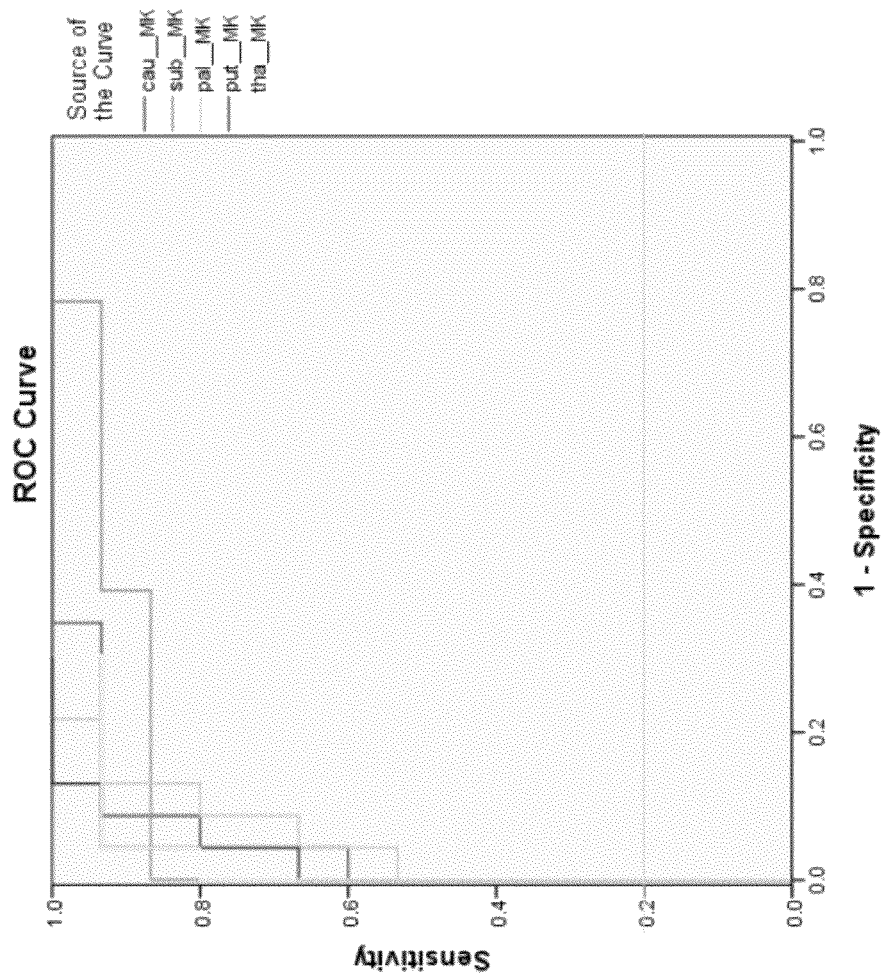

METHOD FOR THE DIAGNOSIS OF NEURODEGENERATIVE DISORDER BY USING DIFFUSION KURTOSIS IMAGING

FIELD OF THE INVENTION

The present invention relates to a method for the diagnosis of neurodegenerative diseases. In particular, the present invention relates to the use of diffusion kurtosis imaging (DKI) in the diagnosis of Parkinson Disease related neurodegenerative disorders, including Parkinson's Disease (PD) and Parkinson plus syndromes.

BACKGROUND OF THE INVENTION

Parkinson's disease (PD) is a progressive neurodegenerative disease, primarily of the substantia nigra in the basal ganglia, that causes resting tremor, bradykinesia, rigidity, postural instability, and gait impairment. PD affects about 1% of the population older than 60 years. It was known to be associated with increased mortality rates, physical disability, non-motor symptoms, and impaired health-related quality of life compared with the quality of life of individuals without PD (Bennett DA, et al., 1996, *N Engl J Med* 334(2): 71-76; Louis ED, et al., 1997, *Arch Neurol* 54(3): 260-264).

Conventional Magnetic Resonance imaging (MRI) characteristics of the substantia nigra in PD include increased iron-related contrast enhancement (Gorell J M, et al., 1995, *Neurology* 45 (6):1138-1143) and loss of signal intensity in the lateral portion of the substantia nigra (Minati L, et al., 2007, *AJNR Am J Neuroradiol* 28(2): 309-313). Although there has been notable progress in studying the correlates of nigral degeneration by means of Magnetic Resonance imaging, techniques that enable accurate differentiation between patients with PD and control subjects remain elusive.

Conventional diffusion coefficients calculated by using the Stejskal-Tanner equation (Stejskal E O, Tanner JE, 1965, *J Chem Phys* 42(1): 288-292) are based on the assumption in a free and unrestricted medium. However, living tissues are known to be heterogeneous in nature and to comprise of multiple compartments. For these reasons, Diffusion Tensor imaging was proposed to measure the directional dependence of in vivo diffusion and was found to be successful. This technique has been shown to be clinically useful in the detection of white matter diseases (Rose SE, et al. 2000, *J Neurol Neurosurg Psychiatry* 69(4): 528-530; Werring DJ, et al., 1999, *Neurology* 52(8): 1626-1632).

In general, water diffusion in living tissue is hindered by interactions with other molecules and cell membranes. Therefore, water in biologic structures often displays non-Gaussian diffusion behavior. MR diffusion kurtosis imaging has been recently proposed as a means of quantifying non-Gaussian water diffusion (Jensen J H, Helpern JA, 2003, Berkeley, Calif.: International Society for Magnetic Resonance in Medicine, 2154; Jensen J H, et al., 2005, *Magn Reson Med* 53(6): 1432-1440; Jensen J H, Helpern J A, 2010, *NMR Biomed* 23(7): 698-710). Diffusion Kurtosis is a dimensionless measure of water diffusion as deviated from Gaussian distribution and reflects the changes in structural complexity. The kurtosis of water diffusion has been shown to be altered in different conditions that affect the central nervous system, including malignancy (Raab P, et al., 2010, *Radiology* 254(3): 876-881) and age-related degeneration (Jensen J H, et al., 2008, *J Magn Reson Imaging* 28 (6): 1345-1350).

Previous studies have shown the feasibility of using the changes of Diffusion Tensor imaging to investigate neuronal loss in different neurodegenerative diseases (Pfefferbaum A, et is al., 2000, *Magn Reson Med* 44(2): 259-268; Wang J J, et al., 2010, *J Magn Reson Imaging* 32(1): 69-75). However, the diffusion tensor imaging findings of Parkinson Disease are controversial (Vaillancourt, D. E., et al., 2009, *Neurology* 72(16): p. 1378; Chan, L. L., et al., 2007, *Journal of Neurology, Neurosurgery & Psychiatry.* 78(12): p. 1383-1468). A precise diffusion model for the gray matter in general and the basal ganglia in particular has not yet been established (Wang J J, et al., 2010, ut supra). Our study results demonstrate that diffusion kurtosis imaging in the basal ganglia can improve the MR based diagnosis of PD.

SUMMARY OF THE INVENTION

This invention is based on the unexpected discovery that diffusion kurtosis imaging in the basal ganglia, as compared with conventional diffusion-tensor imaging, can improve the diagnosis of PD.

In one aspect, the present invention features a diagnostic method for of Parkinson Disease related neurodegenerative disorders, including (but not limited to) Parkinson's disease (PD) and PD plus syndromes. The present invention is characterized by determining the significance of differences in structural complexity in brain by diffusion kurtosis imaging (DKI) analysis. The diagnostic method of this invention comprises the steps of: (a) image acquisition (b) calculation of diffusion kurtosis; (c) selection of regions of interest (ROIs) to obtain the DK data; and (d) comparison of the DK data from patients and control normal subjects.

In one embodiment, the diffusion weighted images consisted of at least 3 diffusion weightings, and for each diffusion weighting, at least 3 diffusion directions; and the mean kurtosis can be calculated from 3 different weightings after averaging the directions. In another embodiment, the diffusion weighted images consisted of data with at least 3 diffusion weightings, and for each diffusion weighting at least 15 diffusion directions; and the mean kurtosis is the magnitude of the calculated diffusion kurtosis tensor.

In one embodiment, the DK data is calculated as a cut of value. In a further embodiment, the images provided from an MR scanner are processed in a computer; and the indices are output after calculation as the clinical condition after diagnosis In another embodiment, the DK is presented as a visual image and the DK data from the region of interest was used for visual diagnosis. In further embodiments, the algorithm based on the visual diagnosis comprises: acquire diffusion weighted images; calculate diffusion tensor and diffusion kurtosis tensor; reconstruct the desired indices from either tensor; and visual assessing the diagnosis using DK as calculated from the diffusion kurtosis tensor.

In certain embodiments of the invention, the selected regions of interest (ROIs) include thalamus, caudate, putamen, globus pallidus, substantia nigra and connected structure. In one embodiment, the selected regions of interest (ROIs) in the method is substantia nigra as applied for diagnosis of Parkinson disease (PD).

In addition, this invention features the use of diffusion kurtosis imaging (DKI) in the diagnosis of Parkinson's disease (PD) and related syndromes, such as Progressive Supranuclear Palsy (PSP), Multiple System Atrophy (MSA), corticobasal degeneration (CBD), and dementia with lewy body (DLB), and the prognosis thereof.

Other features or advantages of the present invention will be apparent from the following drawings and detailed description of several embodiments, and also from the appending claims.

BRIEF DESCRIPTION OF THE DRAWINGS

FIG. 4 shows (a) sensitivity and specificity of MK, FA, mean diffusivity (MD), axial diffusivity (AD), radial diffusivity (RD), and reference standard (Ref) at ROC analysis of bilateral globus pallidus, and (b) mean diffusion index values in patients (gray bars) and control subjects (white bars). FA and MK are dimensionless. Mean, axial, and radial diffusivity values are given in 1000 square millimeters per second. *=Differences between patients and control subjects were significant ($p<0.000416$).

FIG. 6 is a graph showing sensitivity and specificity of MK at Receiver Operative Curve analysis from Regions of Interest (ROI) in caudate (cau), substantia nigra (sub), globus pallidus (pal), putamen (put), and thalamus (tha) in Progressive Supranuclear Palsy (PSP) patients and control normal subjects.

FIG. 7 is a graph showing sensitivity and specificity of MK at Receiver Operative Curve analysis from Regions of Interest (ROI) in caudate (cau), substantia nigra (sub), globus pallidus (pal), putamen (put), and thalamus (tha) in Multiple System Atrophy (MSA) patients and control normal subjects.

DETAILED DESCRIPTION OF THE INVENTION

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Figure 1:
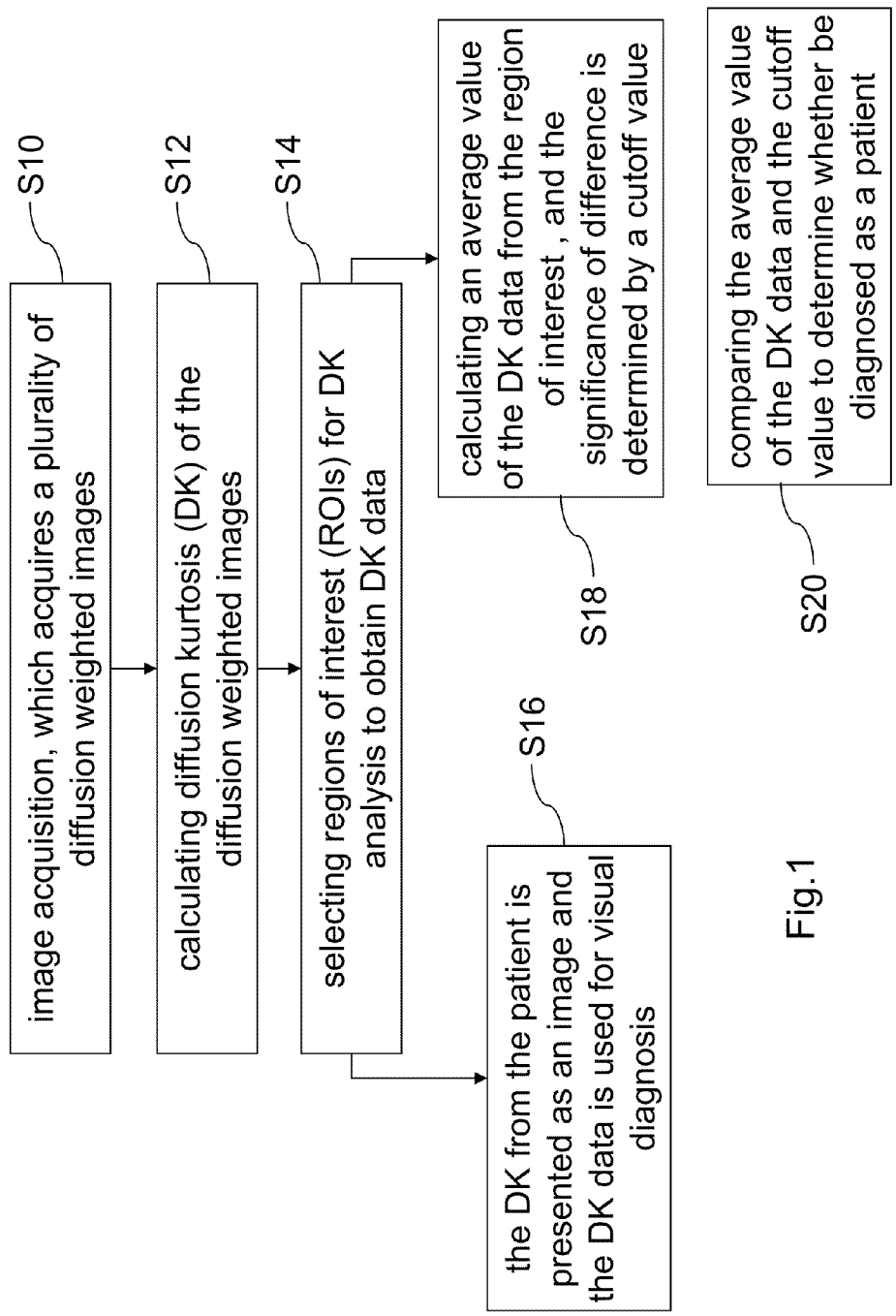
FIG. 1 is a flow chart according to an exemplary embodiment of the diagnostic method of this invention.
Figures 2A, 2B:
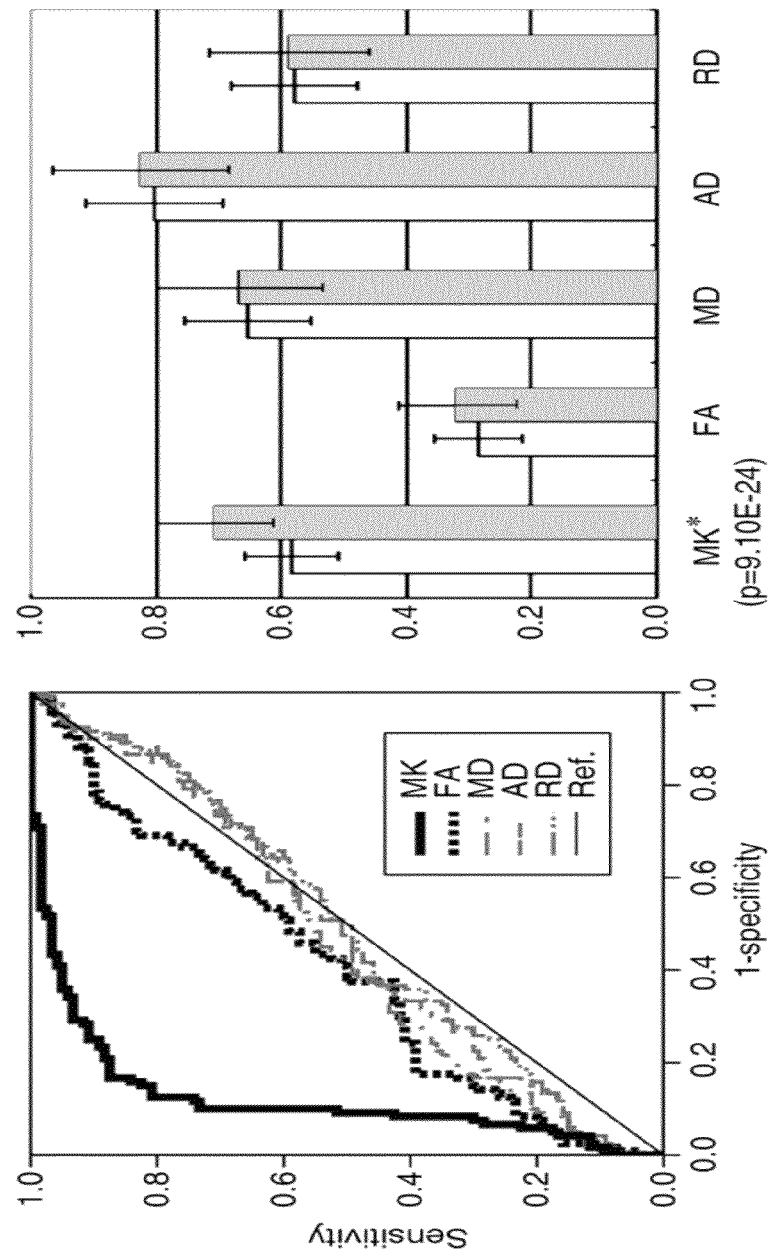
FIG. 2 shows (a) sensitivity and specificity of MK, FA, mean diffusivity (MD), axial diffusivity (AD), radial diffusivity (RD), and reference standard (Ref) at Receiver Operative Characteristic (ROC) analysis of bilateral caudate, and (b) mean diffusion index values in patients (gray bars) and control subjects (white bars). FA and MK are dimensionless. Mean, axial, and radial diffusivity values are given in 1000 square millimeters per second. *=Differences between patients and control subjects were significant ($p<0.000416$).
Figures 3A, 3B:
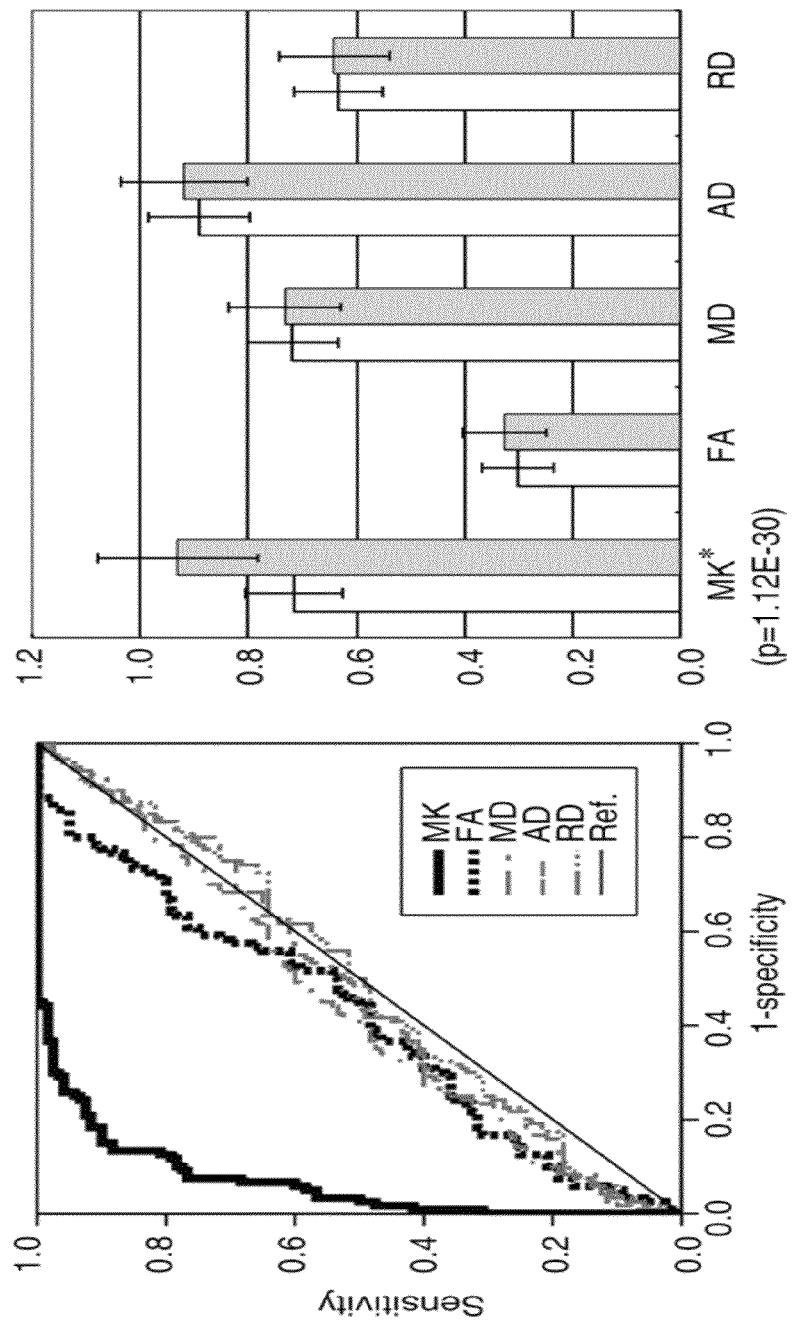
FIG. 3 shows (a) sensitivity and specificity of MK, FA, mean diffusivity (MD), axial diffusivity (AD), radial diffusivity (RD), and reference standard (Ref) at ROC analysis of bilateral putamen, and (b) mean diffusion index values in patients (gray bars) and control subjects (white bars). FA and MK are dimensionless. Mean, axial, and radial diffusivity values are given in 1000 square millimeters per second. *=Differences between patients and control subjects were significant ($p<0.000416$).
Figures 5A, 5B:
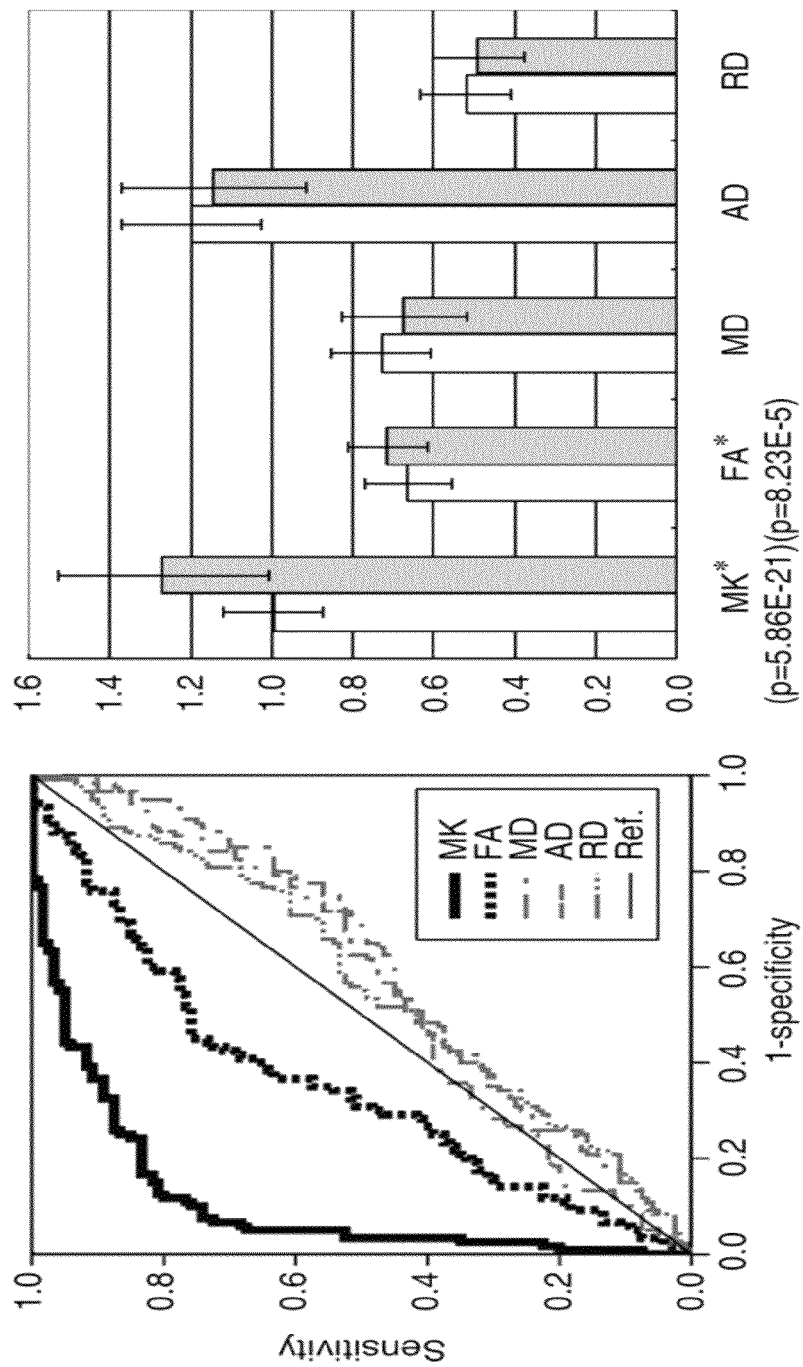
FIG. 5 shows (a) sensitivity and specificity of MK, FA, mean diffusivity (MD), axial diffusivity (AD), radial diffusivity (RD), and reference standard (Ref) at ROC analysis of bilateral substantia nigra bilaterally, and (b) mean diffusion index values in patients (gray bars) and control subjects (white bars). FA and MK are dimensionless. Mean, axial, and radial diffusivity values are given in 1000 square millimeters per second. *=Differences between patients and control subjects were significant ($p<0.000416$).
Figure 8C:
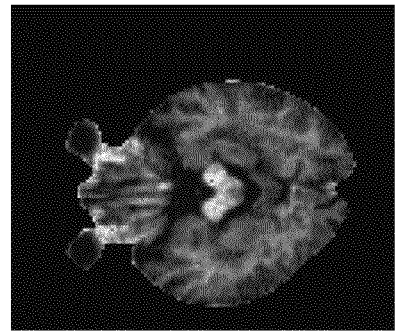
FIG. 8 shows the measured diffusion kurtosis in basal ganglia, as compared to a normal volunteer. The images showed the mean diffusion kurtosis from a normal volunteer (a; b) and a patient with Parkinson's Diease (c; d). The 99 mTc-TRODAT-1 SPECT images in PD patient (e) showed marked decreased activity of dopamine transporter at bilateral striatum.
Figure 8B:
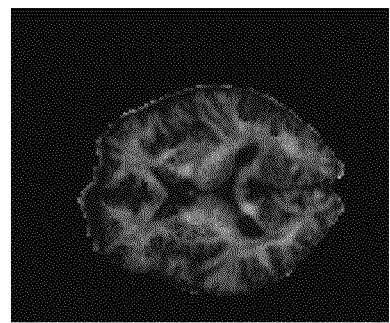
Figure 8A:
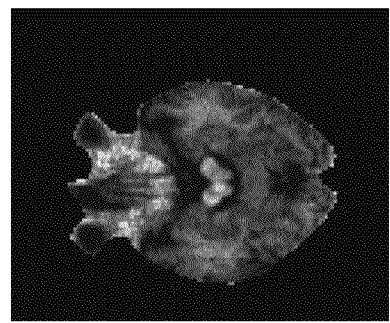
Figure 8E:
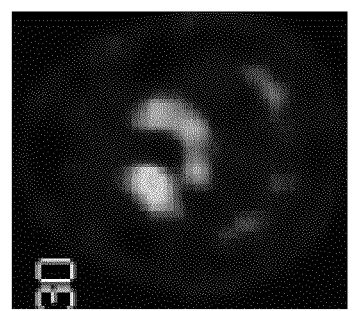
Figure 8D:
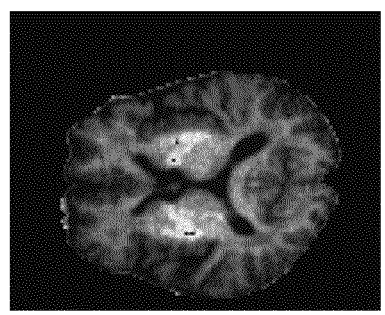

As shown in FIG. 1, it is a flow chart according to an exemplary embodiment of the diagnostic method of the present invention, which comprises the following steps. In S10, the step is image acquisition, which acquires a plurality of diffusion weighted images. Then in S12, calculating diffusion kurtosis (DK) from the diffusion weighted images, wherein the diffusion kurtosis includes mean kurtosis (MK) and indices derived from diffusion kurtosis tensor, included mean kurtosis, axial kurtosis, radial kurtosis and the fractional anisotropy of the diffusion kurtosis tensor. Subsequently, selecting regions of interest (ROIs) for DK analysis to obtain DK data in S14. After the step S14, the method has two pathways, one is going to S16 and the other is going to S18. In S16, the DK from the patient is presented as an image and the DK data is used for visual diagnosis. On the other hand, the method further comprises calculating an average value of the DK data from one of the regions of interest, in S16, and the significance of difference is determined by a cutoff value. Finally, in S18, comparing the average value of the DK data from the region of interest and the cutoff value to determine whether be diagnosed as a patient. In other words, the DK value is calculated, and the significance of difference is determined by a cutoff value, i.e., I calculated the mean from the ROI and compared to a cutoff value. If it is larger than the cutoff, it is significant and is diagnosed as a patient.

EXAMPLE

Between December 2008 and March 2010, a total of 31 patients with PD were en rolled in this prospective study. One patient was excluded because of an incomplete MR examination. All patients met the NINDS-SPSP (National Institute of Neurological Disorders and the Society for Progressive Supranuclear Palsy) (Litvan I, et al., 1996, *Neurology* 47(1): 1-9) or Gelb (Gelb D J, et al., 1999, *Arch Neurol* 56(1): 33-39) criteria for probable PD. All of the patients with PD were receiving optimal pharmacotherapy with levodopa or dopamine agonists. All participants were assessed with use of Hoehn and Yahr staging (Hoehn M M, Yahr M D, 1967, *Neurology* 17(5): 427-442) and the Unified Parkinson's Disease Rating Scale (UPDRS) (Martinez-Martin P, et al., 1994, *Mov Disord* 9(1):76-83) while in the off medication condition (after refraining from taking regular anti-PD medication for 12 hours overnight). Thirty age range-matched healthy subjects who had no history of neuropsychiatric diseases and were recruited from the general population served as community-based control subjects.

The general characteristics of the study participants are presented in Table 1. The examinations were performed with the understanding and written consent of each subject, with approval from the local ethics committee (Chang-Gung Memorial Hospital), and in compliance with national legislation and Declaration of Helsinki guidelines.

TABLE 1

| Characteristic | PD Group (n = 30) | Control Group (n = 30) |
| --- | --- | --- |
| Age (y) | 64.5 ± 3.4 | 65.0 ± 5.1 |
| No. of male/female subjects | 19/11 | 18/12 |
| Disease duration (y) | 5.2 ± 2.0 | NA |
| Median H & Y score*+ | 2 (1-3) | NA |
| UPDRS III-motor subscale score* | 33.6 ± 14.1 | NA |

Note.
Unless otherwise noted, data are mean values ± standard deviation.
NA = not applicable.
*Hoehn and Yahr (H & Y) staging and UPDRS III scores were assessed during the off-medication phase-that is, after the patient has refrained from regular anti-PD medication for 12 hours overnight.
+Numbers in parentheses are the score range.

Image Acquisition

Images were acquired with a 3-T MR unit (Trio a TIM system, Magnetom, Siemens, Erlangen, Germany). T2-weighted fluid attenuated inversion-recovery and three dimensional T1-weighted magnetization prepared rapid acquisition gradient-echo MR images were acquired to rule out concomitant neurologic disorders. For the T2-weighted fluid-attenuated inversion recovery sequence, 9000/85/2500 (repetition time msec/echo time msec/inversion time msec), 34 sections, and a section thickness of 4 mm were used. For the magnetization-prepared rapid acquisition gradient-echo sequence, 2000/4.16 (repetition time msec/echo time msec), a 9° flip angle, and 160 sagittal sections were used.

Diffusion Tensor imaging data were acquired by using a spin-echo echo-planar imaging sequence with the following parameters: repetition time msec/echo time msec=7400/83, a 256-mm$^2$ field of view, and a matrix size 128×128. Diffusion-weighted gradients were applied in 64 noncolinear directions distributed over a full sphere and were optimized by using the static electron repulsion model. A b-value of 1000 sec/mm$^2$ was used. Fifty-six contiguous 2-mm-thick axial sections were obtained to encompass the majority of the brain and led to an isotropic voxel size of 2 mm. The single average acquisition time was 8 minutes 40 seconds.

The mean kurtosis (MK) value was calculated from a series of diffusion-weighted acquisitions with multiple b-values by using the imaging parameters used for the diffusion tensor acquisitions. However, the section thickness was increased because of the increased diffusion weighting in diffusion kurtosis imaging that leads to a reduced signal-to-noise ratio. Fifty-six contiguous 5-mm-thick axial sections were obtained to encompass the majority of the brain down to the cerebrum. The diffusion-weighted gradients were applied in three orthogonal directions, with the b-value varying from 0 to 4000 sec/mm$^2$ in 100 sec/mm$^2$ steps. The single average acquisition time was 7 minutes 39 seconds. The indices in comparison were mean kurtosis (MK), Fractional Anisotropy (FA), Mean/Axial/Radial Diffusivity (MD/AD/RD).

Index Reconstruction and Region-of-Interest Selection

The mean kurtosis could be calculated in the study (Jens H. Jensen, and Joseph A. Helperna, MRI Quantification of Non-Gaussian Water Diffusion by Kurtosis Analysis, NMR Biomed. 2010 August; 23(7): 698-710). Here we provide two illustrative ways of mean kurtosis calculation. In the simplified version, the mean kurtosis calculation comprises: (1). Acquisition of diffusion weighted images of at least 3 diffusion weightings, and for each diffusion weighting, at least 3 diffusion directions are acquired; (2). Average diffusion weighted images along the different directions for each diffusion weighting; (3) and the mean kurtosis is calculate from at least 3 different weightings after averaging the directions. In full diffusion kurtosis tensor, the mean kurtosis calculation comprises: (1). Diffusion weighted images of at least 3 diffusion weightings, and for each diffusion weighting, at least 15 diffusion directions are acquired; (2). Calculate the diffusion kurtosis tensor; and (3) the mean kurtosis is the magnitude of the diffusion kurtosis tensor.

Images were read in an independent fashion by two neuroradiologists with 23 and 31 years of experience. The readers were blinded to the clinical data. Selected regions of interest (ROIs) in the caudate, putamen, globus pallidus, and substantia nigra were placed on non-diffusion-weighted images, with FA (for Diffusion Tensor imaging analysis) or MK (for MK analysis) maps used for reference. ROIs were placed bilaterally on a representative section, along the boundaries of and within the basal ganglia.

Statistical Analysis

All statistical analyses were performed by using the SPSS, version 12.0, software package for Windows (SPSS, Chicago, Ill.). Interrater reliability was assessed by using Pearson correlation coefficients. The Student t test was used to compare the indexes of interest between the patients and the control subjects. We performed ipsilateral, contralateral, and bilateral comparisons between the ROIs on the basis of the laterality of disease onset. A statistical significance threshold of $p<0.000416$ (two-tailed) was used after the traditional Bonferroni correction was applied. Receiver operating characteristic (ROC) curves for each diffusion index were used to determine the cutoff values associated with optimal sensitivity and specificity for distinguishing patients with PD from control subjects. The areas under the ROC curve were used to compare the overall diagnostic performance of the diffusion indexes in each ROI. The associations between the diffusion indexes and disease severity were calculated by using Pearson correlation coefficients. Two-tailed $p<0.05$ was considered to indicate significance.

A high correlation between the independent raters ($P<0.05$ for all ROIs) was observed. The results of ROC curve analysis of ROIs in the caudate (FIG. 2), putamen (FIG. 3), globus pallidus (FIG. 4), and substantia nigra (FIG. 5) are shown. Owing to the unilateral disease onset, results are presented as bilateral ROC analysis data (FIGS. 2(a), 3(a,) 4(a), 5(a)). Mean diffusion index values for the patients and control subjects are shown in FIGS. 2(b), 3(b), 4(b), and 5(b). FA and MK are dimensionless, and diffusivity indexes (axial, radial, and mean diffusivity) are expressed in 1000 square millimeters per second.

For all selected ROIs, the MK of the basal ganglia differed significantly between the patients and control subjects. Among the tensor-derived indexes, the only difference that reached significance was the difference in FA in the substantia nigra ($p<0.000416$). However, there was a large overlap in FA values between the two diagnostic groups. The sensitivity and specificity of the MK at each optimal cutoff point for the selected ROIs are summarized in Table 2. The best diagnostic performance was achieved on the ipsilateral side of the substantia nigra: At a cutoff MK of 1.10, the sensitivity and specificity were 0.92 and 0.87, respectively.

TABLE 2

Diagnostic Sensitivity and Specificity of MK in Different ROIs

| ROI | Cutoff Value | Sensitivity | Specificity |
| --- | --- | --- | --- |
| Caudate | | | |
| Ipsilateral | 0.63 | 0.83 | 0.82 |
| Contralateral | 0.63 | 0.90 | 0.87 |
| Bilateral | 0.63 | 0.84 | 0.83 |

TABLE 2-continued

Diagnostic Sensitivity and Specificity of MK in Different ROIs

| ROI | Cutoff Value | Sensitivity | Specificity |
|---|---|---|---|
| Putamen | | | |
| Ipsilateral | 0.80 | 0.90 | 0.87 |
| Contralateral | 0.80 | 0.87 | 0.87 |
| Bilateral | 0.80 | 0.88 | 0.87 |
| Globus Pallidus | | | |
| Ipsilateral | 1.04 | 0.80 | 0.77 |
| Contralateral | 1.04 | 0.75 | 0.73 |
| Bilateral | 1.05 | 0.73 | 0.77 |
| Substantia nigra | | | |
| Ipsilateral | 1.10 | 0.92 | 0.87 |
| Contralateral | 1.04 | 0.78 | 0.75 |
| Bilateral | 1.07 | 0.83 | 0.83 |

Note.
Data are diagnostic sensitivity and specificity values achieved with the best cutoff MK in the caudate, putamen, globus pallidus, and substantia nigra.

TABLE 3

Areas under ROC Curve and Person Correlation Coefficients for MK Values

| ROI | Area under ROC Curve | Pearson Correlation |
|---|---|---|
| Caudate | | |
| Ipsilateral | 0.87 | 0.812 |
| Contralateral | 0.89 | 0.344 |
| Bilateral | 0.88 | 0.386 |
| Putamen | | |
| Ipsilateral | 0.95 | 0.481 |
| Contralateral | 0.92 | 0.228 |
| Bilateral | 0.94 | 0.169 |
| Globus Pallidus | | |
| Ipsilateral | 0.84 | 0.230 |
| Contralateral | 0.85 | 0.551 |
| Bilateral | 0.85 | 0.191 |
| Substantia nigra | | |
| Ipsilateral | 0.95 | 0.264 |
| Contralateral | 0.85 | 0.479 |
| Bilateral | 0.89 | 0.199 |

Note.
Data are areas under the ROC curve for MK in each ROI and P values of Pearson correlation for associations between MK and UPDRS III scores. No P values indicated significant correlations, The areas under the curve for MK derived at ROC curve analysis are presented in Table 3. Pearson correlation analysis revealed no significant association between the selected ROIs and disease severity. Results of analyses of the association between UPDRS III scores and MK also are presented in Table 3. The area under the ROC curve for the ipsilateral side of both the putamen and the substantia nigra was 0.95. When we performed a combined analysis of the ROIs bilaterally, the area under the ROC curve for the putamen remained similar (0.94). The ipsilateral side of the globus pallidus had the lowest area under the curve (0.84), which was nonetheless higher than this area for all traditional Diffusion Tensor imaging-derived indexes.

According to the results described above, we found that the MK in all major basal ganglia regions was significantly higher in the patients with PD than in the healthy subjects, and demonstrated that diffusion kurtosis imaging in the basal ganglia can improve the MR-based diagnosis of PD. In patient of idiopathic Parkinson's disease, the mean kurtosis in the basal ganglia has significantly improved diagnostic sensitivity and specificity when compared to conventional diffusion indices in differentiating from normal controls. The characterization of non-Gaussian water diffusion with use of diffusion kurtosis can improve the diagnosis of PD, as compared with Diffusion Tensor imaging. On the other hand, the present invention suggests that Diffusion Tensor imaging indexes have limited value in the diagnosis of PD, and MK can be used to distinguish patients from control subjects.

In addition, FIG. 6 and FIG. 7 show the significant differentiation of Mean Kurtosis between normal and patient with Parkinson plus syndrome (PSP/MSA). In this study, a total of 21 patient with a clinical diagnosis of PSP (7 males, 14 females, aged 63±6 years old), were included. The diagnosis of PSP was made according to the established consensus criteria by NINDS-SPSP for probable PSP (Litvan I, et al., 1996, Neurology 47(1): 1-9). A total of 15 patient with a clinical diagnosis of MSA (3 males, 12 females, aged 59±7.3 year old), were included. MSA Patients fulfilled the NINDS Consensus statement for the clinical diagnosis of probable MSA (Gilman, S., et al., Consensus statement on the diagnosis of multiple system atrophy. Journal of the neurological sciences, 1999. 163(1): p. 94-98 & 0022-510X). These results further support the use of diffusion kurtosis imaging (DKI) in the diagnosis of PD related neurodegenerative disorders. Twenty-three age range matched healthy controls (7 male/16 female, aged 63±4.1 years old) were used in the ROC analysis for PSP and MSA.

In summary, the area under the curve (AUC) calculated in receiver operative characteristics analysis of Diffusion Kurtosis Imaging, Diffusion Tensor Imaging and Trodat are listed in the following Table. For AUC in Trodat, the discrimination accuracy between a normal subject and a subject in the prodromal disease stage was AUC=0.924 with PET, compared to 0.863 and 0.831 with simultaneous and sequential SPECT, respectively (from Med. Phys. 35: 3343, 2008).

| | Efficiency | |
|---|---|---|
| Technology | AUC | |
| Diffusion Kurtosis Imaging | 0.95 | |
| Diffusion Tensor Imaging | 0.65 | |
| Trodat | 0.89~0.93 | Disadvange: 1. Radiation dosage 2. Poor spatio-temporal resolution |

Exemplary Diagnosis Case Study

A male subject of 62 year old, with a history of rigidity, bradykinesia, postural instability and little tremor, was diagnosed as Idiopathic Parkinson's Disease and treated with Sinemet for 4 years. Patient responded to medication well. A healthy control subject was included here for the purpose of comparison. Imaging data of both subjects were acquired using the same parameters The neurological examination included poker face, slow swallowing, ataxia, rigidity and bradykinesia. The motor subscale of Unified Parkinson's Disease Rating Scale is 36 and Hoehn & Yahr staging is 2. The subject was prescribed an MR examination using a 3T MR scanner (Trio a TIM system, Magnetom, Siemens, Erlangen, Germany). Diffusion MRI was acquired with a spin-echo echo-planar imaging sequence using the following imaging parameters:
Repitition time/Echo time=7400/83 msec, field of view of 256 mm$^2$, matrix size 128 by 128 and 56 contiguous axial slices of 5 mm thickness. The diffusion-weighted gradients were applied in three orthogonal directions, with the b-value increased from 0 to 4000 sec/mm$^2$ in step of 100 sec/mm$^2$. The single average acquisition time was 7 minutes 39 seconds.

FIG. 8 showed the measured diffusion kurtosis in basal ganglia, as compared to a normal volunteer. The images showed the mean diffusion kurtosis from a normal volunteer (a and b) and a patient with Parkinson's Diease (c and d). A significant increase in diffusion kurtosis can be noticed in the substantia nigra (c) and striatum (d) of the patient, compared to the corresponding location in the normal volunteer (a and b respectively).

Single photon emission computed tomography was acquired 4 hours later after intraveneous injection of 25 mCi of 99 mTc-TRODAT-1. The 99 mTc-TRODAT-1 SPECT images in this PD patient (e) showed marked decreased activity of dopamine transporter at bilateral striatum. In this PD patient, the decreased of TRODAT-1 binding was more obvious in the left striatum (the right of the image according to the nuclear medicine custom) that might be correlated the increased the kurtosis.

This exemplary case study demonstrated the advantage of diffusion kurtosis imaging, as compared to nuclear medicine examination, which can be summarized in the following:
1. diffusion kurtosis imaging does not have radioactivity;
2. diffusion kurtosis imaging does not need the injection of contrast agents nor radioactive tracer;
3. diffusion kurtosis imaging has superior spatial resolution as compared to Trodat images;
4. diffusion kurtosis imaging required a short acquisition time (7 minutes 39 seconds in the current example); and
5. the contrast of diffusion kurtosis imaging is good enough for visual diagnosis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A diagnostic method for Parkinson Disease related neurodegenerative disorders, comprising:
   (a) acquiring a plurality of diffusion weighted images of at least three diffusion weightings and for each diffusion weighting, applying diffusion weighting gradients in three diffusion directions based upon a b-value within the range of 0-4000 sec/mm$^2$ in a plurality of steps;
   (b) averaging the images with the diffusion weighting gradients in all diffusion directions for each of the at least three diffusion weightings; and
   (c) calculating mean kurtosis (MK) value from the at least three diffusion weightings after averaging the at least three diffusion directions to obtain a mean kurtosis (MK) value corresponding to each of the at least three diffusion weightings; and
   (d) comparing the mean kurtosis values from selected regions of interest (ROI);
   wherein the b-value is varying from 0 to 4000 sec/mm$^2$ in 100 sec/mm$^2$ steps.

2. The diagnostic method of claim 1, further comprises:
   calculating an average value of diffusion kurtosis (DK) data from the regions of interest; and
   comparing the average value of the DK data from the regions of interest by a cutoff value for determination of whether a diagnosis of Parkinson Disease is found.

3. The diagnostic method of claim 1, wherein the DK from the patient is presented as an image and the DK data is used for visual diagnosis.

4. The diagnostic method of claim 1, wherein the diffusion kurtosis includes indices derived from diffusion kurtosis tensor, included mean kurtosis, axial kurtosis, radial kurtosis and the fractional anisotropy of the diffusion kurtosis tensor.

5. The diagnostic method of claim 1, wherein the regions of interest (ROIs) are selected from basal ganglia and connected structures.

6. The diagnostic method of claim 5, wherein the basal ganglia is thalamus, caudate, putamen, globus pallidus or substantia nigra.

7. The diagnostic method of claim 5, wherein the connected structure includes thalamus.

8. The diagnostic method of claim 1, wherein the Parkinson Disease related neurodegenerative disorder is movement disorder.

9. The diagnostic method of claim 7, wherein the Parkinson Disease related neurodegenerative disorder is Parkinson's disease (PD).

10. The diagnostic method of claim 7, wherein the Parkinson Disease related neurodegenerative disorder is a PD plus syndrome.

11. The diagnostic method of claim 10, wherein the PD plus syndrome is Progressive Supranuclear Palsy (PSP).

12. The diagnostic method of claim 10, wherein the PD plus syndrome is Multiple System Atrophy (MSA).

13. The diagnostic method of claim 10, wherein the PD plus syndrome is Corticobasal Degeneration (CBD).

14. The diagnostic method of claim 10, wherein the PD plus syndrome is Dementia with LewyBody (DLB).

15. A diagnostic method for Parkinson Disease related neurodegenerative disorders, comprising:
   (a) acquiring a plurality of diffusion weighted images of at least three diffusion weightings and for each diffusion weighting, applying diffusion weighting gradients in at least fifteen diffusion directions based upon a b-value within the range of 0-4000 sec/mm$^2$ in a plurality of steps;
   (b) calculating mean kurtosis (MK) value from the at least three diffusion weightings, wherein the mean kurtosis is calculated by:
   calculating the diffusion kurtosis tensor and/or the diffusion tensor; and
   the mean kurtosis is the magnitude of the diffusion kurtosis tensor; and
   (c) comparing the mean kurtosis values from selected regions of interest (ROI);
   wherein the b-value is varying from 0 to 4000 sec/mm$^2$ in 100 sec/mm$^2$ steps.

* * * * *